United States Patent [19]

Koyama et al.

[11] Patent Number: 5,801,036
[45] Date of Patent: Sep. 1, 1998

[54] MUTANT URICASE, A MUTANT URICASE GENE, A NOVEL RECOMBINANT DNA, AND A PROCESS FOR PRODUCING MUTANT URICASE

[75] Inventors: Yasuji Koyama; Toshio Ichikawa, both of Noda, Japan

[73] Assignee: Kikkoman Corporation, Noda, Japan

[21] Appl. No.: 938,471

[22] Filed: Sep. 29, 1997

Related U.S. Application Data

[62] Division of Ser. No. 701,952, Aug. 23, 1996, Pat. No. 5,700,674.

[30] Foreign Application Priority Data

Aug. 24, 1995 [JP] Japan .................................. 7-216239

[51] Int. Cl.$^6$ .............................. C12N 9/06; C12N 1/20; C12N 15/00; C07H 21/04
[52] U.S. Cl. ................ 435/191; 435/252.33; 435/320.1; 536/23.2; 530/350
[58] Field of Search ............................ 435/191, 252.33, 435/320.1; 536/23.2; 530/350

[56] References Cited

U.S. PATENT DOCUMENTS 5,376,545 12/1994 Yagasaki et al. ..................... 435/191

*Primary Examiner*—Robert A. Wax
*Assistant Examiner*—Tekchand Saidha
*Attorney, Agent, or Firm*—Fish & Richardson P.C.

[57] ABSTRACT

The present invention relates to mutant uricase containing the amino acid sequence of wild-type uricase shown in SEQ ID NO:1 wherein the 165–170th amino acids contain a mutated amino acid sequence, a mutant uricase gene coding for said uricase, a recombinant DNA having said mutant uricase gene integrated into a vector DNA, and a process for producing mutant uricase by culturing a microorganism carrying said recombinant DNA and having the ability to produce mutant uricase in a medium, and then recovering mutant uricase from the culture. The present invention provides stable mutant uricase and the gene coding for said mutant uricase, and further the process of the present invention enables efficient production of stable uricase.

2 Claims, No Drawings

MUTANT URICASE, A MUTANT URICASE GENE, A NOVEL RECOMBINANT DNA, AND A PROCESS FOR PRODUCING MUTANT URICASE

This application is a divisional of U. S. application Ser. No. 08/701,952, filed Aug. 23, 1996, Now U.S. Pat. No. 5,700,674.

FIELD OF THE INVENTION

The present invention relates to mutant uricase, a mutant uricase gene, a novel recombinant DNA, and a process for producing mutant uricase.

BACKGROUND OF THE INVENTION

Uricase is an enzyme catalyzing the following reaction:

$$\text{uric acid} + O_2 + 2H_2O \rightarrow \text{allantoin} + H_2O_2 + CO_2.$$

Because uric acid in serum or urine can be quantified readily and specifically by quantifying hydrogen peroxide formed by the catalytic action of this enzyme, uricase is extremely useful in the field of clinical diagnosis.

Conventionally, uricase has been produced for example by culturing in a medium a microorganism belonging to the genus Escherichia carrying a recombinant DNA having a *Candida utilis*-derived uricase gene inserted into a vector DNA and then recovering uricase from the culture (Japanese Laid-Open Patent Publication No. 317055/93).

However, the uricase obtained in this prior process is disadvantageous in that when stored as a reagent, it is liable to inactivation owing to lack of oxidative stability and thermostability. It has therefore been desired to develop physically and chemically stable uricase.

SUMMARY OF THE INVENTION

The object of the present invention is to provide physically and chemically stable mutant uricase, a gene coding for said mutant uricase, a recombinant having said gene integrated into it, and a process for producing mutant uricase.

As a result of their eager research, the present inventors found that the above problem can be solved by replacing an amino acid sequence around a specific acid in wild-type uricase by a specific sequence by mutation.

That is, the present invention is a mutant uricase gene coding for a polypeptide containing the amino acid sequence of wild-type uricase shown in SEQ ID NO:1 wherein the 165-170th amino acids contain a mutated amino acid sequence. An example of such a mutated amino acid sequence is shown in SEQ ID NO:2.

Further, the present invention is a recombinant DNA having said mutant uricase gene integrated into a vector DNA.

Further, the present invention is a process for producing mutant uricase, which comprises culturing a microorganism belonging to the genus Escherichia carrying said recombinant DNA and having the ability to produce mutant uricase in a medium, and then recovering mutant uricase from the culture.

Further, the present invention is mutant uricase containing the amino acid sequence of wild-type uricase shown in SEQ ID NO:1 wherein the 165-170th amino acids contain a mutated amino acid sequence. An example of such a mutated amino acid sequence is shown in SEQ ID NO:2.

The present invention provides stable mutant uricase and the gene coding for said mutant uricase, and further the process of the present invention enables efficient production of stable uricase.

DETAILED DESCRIPTION OF THE INVENTION

The mutant uricase of the present invention has the amino acid sequence of wild-type uricase shown in SEQ ID NO:1, but with a mutation in the 165-170th amino acids.

Insofar as the desired uricase activity is obtainable, the "mutation" in the present invention is understood as replacement by other amino acids, deletion, or insertion at the 165-170 positions of SEQ ID NO:1. For example, if the 165th and 166th amino acids are tyrosine and asparagine respectively in wild-type uricase, then the 165th and 166th amino acids in the mutant uricase of the present invention may be replaced respectively by any of 18 kinds of amino acids other than tyrosine and asparagine, or tyrosine and/or asparagine may be deleted, or any amino acid may be inserted between tyrosine and asparagine. This also applies to the 167-170th amino acids.

Now, the mutant uricase gene of the present invention is described.

The mutant uricase gene of the present invention that is a gene coding for said mutant uricase can be obtained by genetic engineering means.

To obtain the mutant uricase of the present invention, it is necessary to prepare a wild-type uricase gene and its recombinant DNA. Any wild-type uricase gene can be used and an example is that derived from a microorganism belonging to the genus Candida.

The wild-type uricase gene etc. are prepared by methods known in the art. For example, a wild-type uricase gene and its recombinant DNA can be prepared through cloning from *Candida utilis* ATCC 9950 as a gene source (see Japanese Laid-Open Patent Publication No. 317055/93).

The wild-type uricase is then treated for mutation. This treatment can be carried out in any known method depending on the desired mutation, e.g. by contacting the wild-type uricase gene or a recombinant DNA containing said gene with a chemical agent as mutagen or by ultraviolet radiation, genetic engineering means, protein engineering means etc.

Examples of chemical agents used as mutagen are hydroxylamine, N-methyl-N'-nitro-N-nitrosoguanidine (NTG), nitrous acid, sulfurous acid, hydrazine, formic acid, 5-bromouracil etc.

The conditions for treatment with the mutagen can be selected depending on the type of chemical agent used etc., and are not particularly limited insofar as the desired mutation can actually be induced in the wild-type uricase gene. The desired mutation can generally be induced by treatment with the chemical agent preferably in a concentration of 0.5 to 12 M at a reaction temperature of 20 to 80 ° C. for at least 10 minutes, preferably 10 to 180 minutes. Ultraviolet radiation can also be carried out in a usual manner ("Gendai Kagaku" (Modern Chemistry), pp. 24–30, June issue (1989)).

As protein engineering means, it is possible to use means generally known as site specific mutagenesis. Examples are the Kramer method [Kramer, W. et al., Nucl. Acids Res,12, 9441–9456 (1984); Kramer, W. et al., Methods in Enzymol., 154, 350–367 (1987); Bauer, C. E. et al., Gene, 37, 73–81 (1985)], the Eckstein method [Taylor, J. W. et al., Nucleic Acids Res., 13, 8749–8764 (1985); Taylor, J. W. et al., Nucleic Acids Res. 13, 8765–8785 (1985); Nakamaye K., et al. , Nucleic Acids Res. 14, 9679–9698 (1986)]; and the Kunkel method [Kunkel, T. A., Proc. Natl. Acad. Sci.82, 488–492 (1985); Kunkel, T. A., et al., Methods in Enzymol., 154, 367–382 (1987)].

In addition to the aforementioned gene modification methods, organic synthesis or enzymatic synthesis can also be used to directly synthesize the desired modified uricase gene. The desired uricase gene thus obtained can be determined and confirmed by a method such as the chemical modification method of Maxam and Gilbert [Maxam and Gilbert, Methods in Enzymol., 65, 499–560 (1980)] or the dideoxynucleotide chain termination method using M13 phage [Messing et al., Gene,19, 269–276 (1982)].

By the aforementioned mutation means, it is possible to obtain the mutant uricase gene coding for a polypeptide containing the amino acid sequence of wild-type uricase wherein the 165–170th amino acids contains a mutated amino acid sequence. An example of such an amino acid sequence where the 165–170th amino acids are mutated is shown in SEQ ID NO:2. Two or more codons coding for the same amino acid (degenerate codons) may be contained in said gene.

The mutant uricase gene thus obtained can be integrated in a usual manner into a vector such as bacteriophage, cosmid, or plasmid for transformation of procaryotic or eucaryotic cells, to transform or transduce a host compatible with the vector.

Examples of hosts are microorganisms belonging to the genus Escherichia, including *E. coli* JM101 (ATCC 33876) ,*E. coli* DH1 (ATCC 33849),*E. coli* HB101 (ATCC 33694), and *E. coli* XL1-blue (purchased from Funakoshi K.K., Japan). If such a microorganism is selected, a transformed or transduced strain can be obtained by transformation according to e.g. the Hanahan method (DNA Cloning, 1, 109–135 (1985)) or transduction according to e.g. the method described in Molecular Cloning, pp. 256–268, Cold Spring Harbor Laboratory (1982).

The resulting strain can be screened for the target transformant i.e. the strain belonging to the genus Escherichia carrying the recombinant DNA having the mutant uricase gene inserted into a vector DNA and having the ability to produce the mutant uricase.

The novel recombinant DNA can be purified from the transformant by a conventional method described in e.g. Current Protocols in Molecular Biology (Wiley Interscience, 1989) unit 1.7.

From the recombinant DNA, the DNA containing the mutant uricase gene can be obtained by treating the plasmid DNA with a restriction enzyme such as EcoRI at 30 to 40° C., preferably around 37° C., for 1 to 24 hours, preferably about 2 hours and then subjecting the reaction solution to agarose gel electrophoresis as described in Molecular Cloning, p. 150, Cold Spring Harbor Laboratory (1982).

Now, the production of the mutant uricase of the present invention is described.

The mutant uricase of the present invention can be obtained by culturing the transformant obtained as described above and purifying uricase from the culture.

Culture may be carried out in a conventional solid medium, but preferably in a liquid medium.

As the medium for culturing said strain, mention may be made of a medium containing one or more nitrogen sources such as yeast extract, trypton, peptone, meat extract, corn steep liquor and exudate of soybean or wheat bran, one or more inorganic salts such as sodium chloride, dipotassium hydrogen phosphate, potassium dihydrogen phosphate, magnesium sulfate, magnesium chloride, ferric chloride, ferric sulfate and manganese sulfate, and if necessary sugars or carbohydrates and vitamins.

The initial pH of medium is adjusted preferably in the range of pH 7–9. Culture is continued for 4 to 24 hours, preferably 6 to 20 hours and at 30 to 42° C., preferably around 37° C., by submerged aeration culture, shake culture, or stationary culture.

After culture is finished, the mutant uricase can be recovered from the culture by conventional enzyme purification means. For example, the enzyme can be extracted by disrupting the microorganisms by ultrasonication or grinding or treatment with lytic enzyme such as lysozyme or released by autolysis of the microorganisms in the presence of a solvent such as toluene optionally under shaking.

Insolubles are removed from the extract by filtration or centrifugation and if necessary nucleic acids are removed by adding streptomycin sulfate, protamine sulfate, manganese sulfate etc. Then, the solution is fractionated with ammonium sulfate, alcohol, acetone etc., and the precipitates are recovered as crude enzyme. This crude enzyme is then purified by chromatography, electrophoresis etc., for example gel filtration on Sephadex, Ultrogel, Biogel etc., adsorption-elution on ion exchanger, electrophoresis on polyacrylamide gel etc., adsorption-elution on hydroxyapatite, sedimentation by sucrose density gradient centrifugation etc., affinity chromatography, and fractionation through molecular sieve membrane, hollow fiber membrane etc. These can be suitably selected or combined to purify the crude enzyme.

Whether the amino acid sequence of the purified mutant uricase undergoes the desired mutation or not can be confirmed by conventional amino acid analysis, for example the Edman method for automatic amino acid sequencing. The activity of the mutant uricase may be compared with that of wild-type uricase by use of the uricase activity remaining as an index of mutation after heating at 60° C. for 15 minutes.

EXAMPLES

The present invention is illustrated by the following examples which however are not intended to limit the scope of the present invention.

[Example 1]

1. Preparation of recombinant plasmid DNA pUO1001

Recombinant plasmid DNA pUOX101 (deposited as FERM BP-3842) described in Japanese Laid-Open Patent Publication No. 317055/93 was cleaved with restriction enzymes BalI and EcoRI and then separated by agarose gel electrophoresis to give an about 700 bp DNA fragment. This fragment was inserted into pUC119 previously cleaved with HincII and EcoRI to construct recombinant plasmid DNA pUO1001. The nucleotide sequence of the wild-type uricase gene from *E. coli* JM109 (pUOX101) and its coding amino acid sequence are shown in SEQ ID NOS: 3 and 1, respectively.

2. Acquisition of mutant uricase

Recombinant plasmid DNA pUO1001 was transformed into *E. coli*CJ236 (purchased from Bio-Rad) and a single-stranded DNA was obtained from recombinant plasmid DNA pUO1001 in usual manner. Site specific mutagenesis was carried out using a Muta-Gene in vitro mutagenesis kit (produced by Bio-Rad) with the single-stranded DNA as a template and the oligonucleotide shown in SEQ ID NO:4 as a primer.

The mutant DNA thus obtained was transformed into *E. coli* XL1-Blue (purchased from Funakoshi). Recombinant plasmid DNA pUO1002 was prepared in a usual manner from the transformant.

pUO1002 was cleaved with restriction enzymes BstXI and XhoI and then separated by agarose gel electrophoresis to give a 310 bp DNA fragment. This fragment was inserted into pUOX101 previously cleaved with BstXI and XhoI then transformed into *E coli* XL1-Blue. The resulting plasmid DNA was designated pUOX101β The resulting *E. Coli* XL1-Blue (pUOX101β) has been deposited as FERM BP-5204 with the National Institute of Bioscience and Human-Technology, Agency of Industrial Science and Technology, Japan.

3. Properties of the mutant strain

The *E. coli* XL1-Blue (pUOX101β) thus obtained was incubated at 37 °C. for 20 hours in TY medium (1 % (W/V) trypton, 0.5 % (W/V) yeast extract, 0.5 % (W/V) common salt) containing 1 mM IPTG and 100 μ g/ml ampicillin, then disrupted by ultrasonication, and centrifuged to give a crude enzyme solution.

0.1 ml of the crude enzyme solution was placed in an Eppendorf tube and heated at 60° C. for 15 minutes. The remaining enzyme activity was determined according to the method described in Agri. Biol. Chem., vol. 31, no. 11, pp. 1256–1264 (1967).

The results are shown in Table 1. For comparison, the value of *E. coli* JM109 (pUOXO101) (wild-type) is also shown. In the table, the values in the parentheses indicate the proportion of the enzyme activity remaining after heat treatment to the activity in the untreated crude enzyme solution.

TABLE 1

|  | no treatment | treatment at 60° C., 15 min. |
|---|---|---|
| *E. coli* JM109 (pUOX101) wild-type | 0.738 U/ml (100%) | 0.048 U/ml (6.5%) |
| *E. coli* XL1-Blue (pUOX101β) mutant | 0.807 U/ml (100%) | 0.856 U/ml (106%) |

TABLE 1

|  | no treatment | treatment at 60° C., 15 min. |
|---|---|---|
| *E. coli* JM109 (pUOX101) wild-type | 0.738 U/ml (100%) | 0.048 U/ml (6.5%) |
| *E. coli* XL1-Blue (pUOX101β) mutant | 0.807 U/ml (100%) | 0.856 U/ml (106%) |

We claim:

1. Mutant uricase having the amino acid sequence of wild-type uricase shown in SEQ ID NO:1, wherein the 165–170th amino acids contain a mutated amino acid sequence.

2. The mutant uricase according to claim 1, wherein said mutated amino acid sequence is shown in SEQ ID NO:2.

* * * * *